United States Patent [19]

Marlett

[11] Patent Number: 4,665,207

[45] Date of Patent: May 12, 1987

[54] PREPARATION OF AMINE ALANE COMPLEXES

[75] Inventor: Everett M. Marlett, Baton Rouge, La.

[73] Assignee: Ethyl Corporation, Richmond, Va.

[21] Appl. No.: 782,972

[22] Filed: Oct. 2, 1985

[51] Int. Cl.$^4$ .............................................. C07F 5/06
[52] U.S. Cl. .................................................. 556/176
[58] Field of Search ........................................ 556/176

[56] References Cited

U.S. PATENT DOCUMENTS

| | | |
|---|---|---|
| 2,680,059 | 6/1954 | Bragdon . |
| 3,326,955 | 6/1967 | Brendel et al. ...................... 556/176 |
| 3,535,107 | 10/1970 | Nelson et al. .................... 556/176 X |
| 3,541,125 | 11/1970 | Sims .................................. 556/176 |
| 3,891,686 | 6/1975 | Ehrlick et al. ...................... 556/176 |
| 3,926,833 | 12/1975 | Hoffman et al. . |
| 3,983,150 | 9/1976 | Casensky et al. ................... 556/176 |
| 4,006,095 | 2/1977 | Hoffman et al. ................ 556/176 X |
| 4,022,809 | 5/1977 | Cucinella et al. ................... 556/176 |
| 4,064,153 | 12/1977 | Cucinella et al. ............... 556/176 X |
| 4,239,692 | 12/1980 | Dozzi et al. .................... 556/176 X |

OTHER PUBLICATIONS

Beattie, et al., J.C.S. (Dalton), pp. 528, 534 (1979).
Chemical Abstracts vol. 84 58605b (1976).
Chemical Abstracts vol. 83 179913p (1975).
Chemical Abstracts vol. 82 179795f (1975).
Dilts, et al., "The Composition of Complex Metal Hydrides in Polar Solvents", Inorg. Chem., vol. 9, No. 4, Apr. (1970), pp. 855–862.

Primary Examiner—Helen M. S. Sneed
Attorney, Agent, or Firm—Donald L. Johnson; John F. Sieberth; Robert A. Linn

[57] ABSTRACT

A process for producing complexes of alane and tertiary amines. Sodium aluminum tetrahydride is reacted with sodium aluminum tetrachloride in the presence of a tertiary amine in an aromatic hydrocarbon reaction medium that is not a solvent for either of the reactants. The tertiary amine alane reaction products are typically soluble in the hydrocarbon reaction medium and readily recoverable.

27 Claims, No Drawings

PREPARATION OF AMINE ALANE COMPLEXES

BACKGROUND OF THE INVENTION

This invention relates in general to the amine complexes and in particular to complexes of tertiary amines with alane ($AlH_3$). Alane, that is aluminum trihydride, has in the past been produced from the reaction of $LiAlH_4$ and $AlCl_3$ in ethers. Also known is the production of a dimethyl ether solution of alane from the reaction of LiH and $AlCl_3$ in dimethyl ether, catalyzed by $NaAlH_4$.

Amines may be used to produce amine alanes for subsequent synthesis. For example, $LiAlH_4$ may be reacted with a trialkyl amine HCl complex to precipitate LiCl and form a trialkyl amine alane complex.

Amine alane complexes may be used to produce silane by reaction of the amine alane complex with a halosilane such as the chlorosilanes, especially silicon tetrachloride. The amine alane complexes of the invention may also be used for a variety of reducing reactions where a source of hydrogen is required.

SUMMARY OF THE INVENTION

This invention provides a process for making amine alane complexes from alkali metal aluminum tetrahalides or alkaline earth metal aluminum tetrahalides.

Despite the lack of solubility of the reactant hydride and general insolubility of the other reactant, a halide, in a hydrocarbon or tertiary amine reaction medium, the reaction is particularly effective in either medium so long as a tertiary amine is present. I have found that, surprisingly, the solids react almost quantitatively in a hydrocarbon reaction medium when a tertiary amine is also present. The amine alane product and reaction medium may be chosen such that the product dissolves in the medium and does not coat the reactants to prevent further reaction. Also, the salt by-products precipitate and are readily recovered and disposed of or otherwise used. In fact, one typical by-product of the reaction is sodium chloride which is easily handled and is ecologically acceptable.

DESCRIPTION OF THE PREFERRED EMBODIMENTS

A preferred embodiment of the invention is a process for preparing amine alane complexes comprising reacting:

(a) about p mole parts $M(AlX_4)_n$ wherein X is Cl or Br, M is alkali metal or alkaline earth metal, n is 1 and p is 1 when M is alkali metal or n is 2 and p is 0.5 when M is alkaline earth metal; and (b) about q mole parts $L(AlH_4)_r$ wherein L is alkali metal or alkaline earth metal, q is 3 and r is 1 when L is alkali metal or q is 1.5 and r is 2 when L is alkaline earth metal; in the presence of (c) about 4 mole parts of a complexing tertiary amine in a liquid reaction medium selected from hydrocarbons and tertiary amines nonsolvent for the reactants of (a) and (b) and forming a complex of said tertiary amine and $AlH_3$.

Another preferred embodiment of the invention is a process for producing amine alane complexes comprising reacting a tetrahalide of the formula $MAlX_4$ wherein X is Br or Cl and M is alkali metal with an alkali metal aluminum tetrahydride in the presence of a complexing tertiary amine in a liquid reaction medium selected from hydrocarbons and tertiary amines not solvent for said tetrahalide or said alkali metal aluminum tetrahydride and forming a tertiary amine $AlH_3$ complex.

According to the invention, a metal aluminum chloride or bromide is reacted with a metal aluminum tetrahydride in a tertiary amine liquid reaction medium or in a liquid hydrocarbon medium in the presence of a complexing tertiary amine to form a complex of the tertiary amine and alane, $AlH_3$. Surprisingly, these solids react almost quantitatively in tertiary amines or in hydrocarbons when a complexing tertiary amine is present. Both the metal aluminum halide and the metal aluminum tetrahydride reactants per se are essentially insoluble in tertiary amines and hydrocarbons. Partial dissociation of these compounds may occur in the presence of strong amines and give the appearance of slight solubility.

Of course, the reaction progress is enhanced by mixing and the provision of stoichiometric proportions of reactants.

The amine alane product readily dissolves in many tertiary amines and hydrocarbons and therefore does not coat the reactants present or otherwise hinder the reaction. Furthermore, the invention provides a salt by-product which is very easily recovered since it precipitates from the tertiary amines or hydrocarbon reaction medium for further use or disposal. Finally, the product may be readily recovered from the hydrocarbon reaction medium by any known method such as solvent stripping, crystallization, or the like. Alternatively, the amine alane solution in tertiary amine or in hydrocarbon may be used for subsequent reaction to form another product. A preferred use of the amine alane complex in hydrocarbon is the reaction with a silicon halide to prepare silane or halosilanes.

The halide reactants usable according to the invention may be represented by the formula $M(AlX_4)_n$ wherein X is chlorine or bromine, M is alkali metal or alkaline earth metal, and n is 1 when M is alkali metal or 2 when M is alkaline earth metal. Suitable alkali metals include sodium, lithium, potassium, rubidium, and cesium. Usable alkaline earth metals include beryllium, magnesium, calcium, strontium, and barium. Therefore, halide reactants of the invention include the following compounds: $NaAlCl_4$, $NaAlBr_4$, $LiAlCl_4$, $LiAlBr_4$, $KAlCl_4$, $KAlBr_4$, $Mg(AlCl_4)_2$, $Mg(AlBr_4)_2$, $Ca(AlCl_4)_2$, $Ca(AlBr_4)_2$, and the like.

Metal aluminum tetrahydride reactants suitable for the invention include those alkali metals such as sodium, lithium, potassium, rubidium, and cesium as well as those alkaline earth metal aluminum tetrahydrides of beryllium, magnesium, calcium, strontium, and barium. Therefore, suitable hydride reactants according to the invention are $NaAlH_4$, $LiAlH_4$, $KAlH_4$, $RbAlH_4$, $Mg(AlH_4)_2$, $Ca(AlH_4)_2$, and the like.

The preferred halide reactant of the invention is $NaAlCl_4$. The preferred hydride reactant of the invention is $NaAlH_4$. Of course any of the described halides or hydrides which provide an amine alane product when reacted in a tertiary amine or hydrocarbon medium in the presence of a complexing tertiary amine, are suitable for the invention.

A broad variety of tertiary amines are suitable for the invention as mediums or reactant/complexing agents so long as they complex with $AlH_3$ in a tertiary amine or hydrocarbon reaction medium. The tertiary amines of the invention include the trialkylamines and polyamines. Suitable trialkylamines include the tri-lower alkylamines such as trimethylamine, triethylamine, tripropylamine, tributylamine, and the like. Trimethylamine is a gas at room temperature and is therefore more difficult to use in the preparation of an amine alane complex. However, where desirable, trimethylamine forms a strong complex with $AlH_3$. Triethylamine is the most preferred amine of the invention for both complexing and as a medium. It forms a complex with $AlH_3$ of moderate strength which makes the complex suitable for further reaction and utilization of the complex.

Among the tertiary polyamines usable with the invention are N,N,N',N'-tetramethylethylenediamine and 1,4-diazabicyclo-[2.2.2]-octane (Dabco or triethylenediamine). Other tertiary mono- and polyamines are also suitable such as ethyl dimethylamine, diethylmethylamine, dimethylpropylamine, N,N,N',N'-tetramethyldiaminomethane, quinuclidine, methyl-1,4-diazabicyclo[2.2.2]octane, and the like.

A broad variety of hydrocarbon reaction mediums may be usable according to the invention. Aromatic hydrocarbons are a preferred class of liquid reaction medium, toluene being a highly preferred liquid reaction medium. Suprisingly, amine alane complexes can be readily prepared in toluene and other hydrocarbon reaction mediums from metal aluminum tetrahydrides and the halide reactants described above. Of course agitation of the reaction mixture is highly preferred since it provides a higher degree of contact between the reactants in the hydrocarbon reaction medium. Alkali metal chloride or bromide or alkaline earth metal dichloride or dibromide precipitate readily as a by-product from the reaction mixture as the product is readily formed and generally dissolved in hydrocarbon reaction medium.

Other usable aromatic hydrocarbons according to the invention are benzene, ethylbenzene, propylbenzene, butylbenzene, meta-xylene, para-xylene, ortho-xylene, 1,2-diethylbenzene, 1,3-diethylbenzene, 1,4-diethylbenzene, 1,3-dipropylbenzene, 3-propyltoluene, 4-ethyltoluene, 4-propyltoluene, 4-butyltoluene, the trimethylbenzenes, and trialkylbenzenes generally. Also suitable are liquid polycyclic aromatic hydrocarbons such as 1-methylnaphthalene, tetrahydronaphthalene, and the like.

Another class of hydrocarbon reaction medium usable with the invention include the alkanes such as pentane, hexane, heptane, octane, nonane, decane, undecane, dodecane, and the like.

The suitable hydrocarbon reaction mediums of the invention are generally innocuous to the inventive reaction process. That is, they do not interfere with the formation of the amine alane complexes of the invention. Similarly, the tertiary amine reaction mediums are innocuous except for that stiochiometric portion which complexes with the alane.

In view of the above, the preferred product of the invention is the complex of triethylamine with $AlH_3$.

Preferably, a stoichiometric amount of reactants are used. That is, three tetrahydride equivalents and four amine equivalents should be present for each tetrahalide equivalent. Thus, if one mole part of alkali metal aluminum tetrahalide is reacted, then three mole parts of an alkali metal aluminum tetrahydride (or 1.5 mole parts of an alkaline earth metal aluminum di(tetrahydride)) and four mole parts tertiary amine should be used. For an alkaline earth metal aluminum tetrahalide, twice as much hydride and amine are required for stoichiometry.

There is no critical sequence for carrying out the process of the invention. The hydride reactant is often available in a hydrocarbon slurry and it may be convenient to weigh the complexing tertiary amine in a portion of hydrocarbon. Thus the reaction may be carried out by adding the halide solid reactant to the hydride slurry followed by addition of amine in additional hydrocarbon. The reaction may be effected at room temperature and no appreciable exotherm is observed. The product slurry of the invention may be filtered and the product cake may be rinsed with additional hydrocarbon. Generally, the filtrate is clear with few contaminants.

The reaction may be carried out at subatmospheric, superatmospheric, or atmospheric pressures, with little effect on the yield of the reaction.

A broad range of temperatures may be used to carry out the inventive process for most reactants. Any temperature may be used so long as the halide and hydride reactants may be combined with the reaction medium in a liquid state. The reaction may be carried out over a broad range of temperatures ranging from that low temperature where the reaction will proceed to a high temperature which is short of the point where the reaction product amine alane decomposes, depending upon the amine chosen. A suitable range of reaction temperature is about $-50°$ C. to about $100°$ C., a more preferred range is about $0°$ C. to $65°$ C.

A better understanding of the invention will be had by a review of the following examples.

EXAMPLE $NaAlCl_4$ was prepared by reaction of reagent grade (98% purity) $AlCl_3$ and NaCl. $NaAlCl_4$, 3.85 grams (0.020 mol), was mixed with 3.67 grams (90.4% pure, 0.060 mol) $NaAlH_4$ in a 100 mL round bottom flask. About 8.36 grams (0.08 mol) triethylamine was combined with 38.0 grams toluene and added to the solid reactants in the flask at $20°$ C. The mixture was stirred with a magnetic stirrer for three hours. The reaction mixture was filtered and the NaCl by-product removed to give a water white solution of the product in toluene. The product solution weighed 46.58 grams. Analysis by gas evolution and soluble aluminum showed a 57% yield of $AlH_3 \cdot N(C_2H_5)_3$.

The reaction was repeated three times using a by-product stream of $NaAlCl_4$ of over 90% purity. The respective reactant portions were 3.84 grams (0.02 mol) $NaAlCl_4$, 3.70 grams (92.0% pure, 0.060 mol) $NaAlH_4$, 39.8 grams toluene and 8.18 grams (0.08 mol) triethylamine. After four hours in each run at $0°-25°$ C. the yields were 89%, 73%, and 89%. The yield could be increased over 90% by allowing the reaction to proceed for about six hours.

I claim:

1. A process for preparing amine alane complexes comprising reacting:
    (a) about p mole parts $M(AlX_4)_n$ wherein X is Cl or Br, M is alkali metal or alkaline earth metal, n is 1 and p is 1 when M is alkali metal or n is 2 and p is 0.5 when M is alkaline earth metal; and
    (b) about q mole parts $L(AlH_4)_r$ wherein L is alkali metal or alkaline earth metal, q is 3 and r is 1 when L is alkali metal or q is 1.5 and r is 2 when L is alkaline earth metal; in the presence of
    (c) about 4 mole parts of a complexing tertiary amine in a liquid reaction medium selected from innocuous hydrocarbons and tertiary amines nonsolvent for reactants (a) and (b);

thereby forming a complex of said tertiary amine and $AlH_3$.

2. The process of claim 1 wherein said liquid reaction medium is an innocuous hydrocarbon and said hydrocarbon is an aromatic hydrocarbon.

3. A process for producing amine alane complexes comprising reacting a tetrahalide of the formula $MAlX_4$ wherein X is Br or Cl and M is alkali metal with an alkali metal aluminum tetrahydride in the presence of a complexing tertiary amine in a liquid reaction medium selected from innocuous hydrocarbons and tertiary amines not a solvent for said tetrahalide or said alkali metal aluminum tetrahydride, thereby forming a tertiary amine.$AlH_3$ complex.

4. A process for producing amine alane complexes comprising reacting a tetrahalide of the formula $MAlX_4$ wherein X is Br or Cl and M is alkali metal with an alkali metal aluminum tetrahydride in the presence of a complexing trialkylamine in a liquid reaction medium selected from innocuous hydrocarbons and tertiary amines not a solvent for said tetrahalide or said alkali metal aluminum tetrahydride and forming a trialkylamine.$AlH_3$ complex.

5. A process for preparing amine alane complexes comprising reacting:
(a) about p mole parts $M(AlX_4)_n$ wherein X is Cl or Br, M is alkali metal or alkaline earth metal, n is 1 and p is 1 when M is alkali metal or n is 2 and p is 0.5 when M is alkaline earth metal; and
(b) about q mole parts $L(AlH_4)_r$ wherein L is alkali metal or alkaline earth metal, q is 3 and r is 1 when L is alkali metal or q is 1.5 and r is 2 when L is alkaline earth metal; in the presence of
(c) about 4 mole parts of a complexing trialkylamine in a liquid reaction medium selected from innocuous hydrocarbons and tertiary amines nonsolvent for the reactants (a) and (b);

thereby forming a complex of said trialkylamine and $AlH_3$.

6. The process of claim 4 wherein said liquid reaction medium is an innocuous hydrocarbon.

7. The process of claim 6 wherein said innocuous hydrocarbon is an aromatic hydrocarbon.

8. The process of claim 7 wherein said aromatic hydrocarbon is toluene.

9. The process of claim 5 wherein M is alkali metal.

10. The process of claim 9 wherein said alkali metal is sodium.

11. The process of claim 10 wherein X is Cl.

12. The process of claim 2 wherein said aromatic hydrocarbon is toluene.

13. The process of claim 1 wherein M is alkali metal.

14. The process of claim 13 wherein said alkali metal is sodium.

15. The process of claim 14 wherein X is Cl.

16. The process of claim 1 wherein X is Cl.

17. The process of claim 1 wherein the said tertiary amine forms a complex with $AlH_3$ that is soluble in said hydrocarbon.

18. The process of claim 17 wherein said hydrocarbon is toluene.

19. The process of claim 5 wherein said trialkylamine is triethylamine.

20. The process of claim 5 wherein said reacting is carried out at about 0°-100° C.

21. The process of claim 5 wherein said liquid reaction medium is a tertiary amine.

22. The process of claim 3 wherein said liquid reaction medium is an aromatic hydrocarbon.

23. The process of claim 22 wherein said complexing tertiary amine is triethylamine.

24. The process of claim 33 wherein $NaAlCl_4$ is reacted with $NaAlH_4$.

25. The process of claim 5 wherein said complexing tertiary amine is triethylamine.

26. The process of claim 25 wherein said liquid reaction medium is toluene.

27. The process of claim 26 wherein about one mole part $NaAlCl_4$ is reacted with about three mole parts $NaAlH_4$ in the presence of at least about four mole parts triethylamine.

* * * * *

UNITED STATES PATENT AND TRADEMARK OFFICE
CERTIFICATE OF CORRECTION

PATENT NO. : 4,665,207

DATED : MAY 12, 1987

INVENTOR(S) : Everett M. Marlett

It is certified that error appears in the above-identified patent and that said Letters Patent is hereby corrected as shown below:

Column 6, line 1, "claim 4" should read -- claim 5 --.

Column 6, line 33, "claim 33" should read -- claim 3 --.

Signed and Sealed this

Eighteenth Day of August, 1987

*Attest:*

DONALD J. QUIGG

*Attesting Officer*  *Commissioner of Patents and Trademarks*